United States Patent
Ackermann, Jr. et al.

(10) Patent No.: US 9,008,800 B2
(45) Date of Patent: Apr. 14, 2015

(54) SEPARATED-INTERFACE NERVE ELECTRODE

(75) Inventors: Douglas Michael Ackermann, Jr., Palo Alto, CA (US); Kevin Kilgore, Avon Lake, OH (US); Niloy Bhadra, Cleveland Heights, OH (US); Narendra Bhadra, Chesterland, OH (US)

(73) Assignee: Case Western Reserve University, Cleveland, OH (US)

( * ) Notice: Subject to any disclaimer, the term of this patent is extended or adjusted under 35 U.S.C. 154(b) by 325 days.

(21) Appl. No.: 12/949,074

(22) Filed: Nov. 18, 2010

(65) Prior Publication Data

US 2011/0160798 A1 Jun. 30, 2011

Related U.S. Application Data

(60) Provisional application No. 61/263,592, filed on Nov. 23, 2009.

(51) Int. Cl.
*A61N 1/00* (2006.01)
*A61N 1/05* (2006.01)
*A61N 1/04* (2006.01)
*A61N 1/32* (2006.01)
*A61N 1/36* (2006.01)

(52) U.S. Cl.
CPC ............. *A61N 1/0551* (2013.01); *A61N 1/0436* (2013.01); *A61N 1/0556* (2013.01); *A61N 1/325* (2013.01); *A61N 1/36067* (2013.01); *A61N 1/36103* (2013.01)

(58) Field of Classification Search
CPC .......................... A61N 1/0551; A61N 1/0556
USPC ........................... 607/1–3, 115–118, 120, 46
See application file for complete search history.

(56) References Cited

U.S. PATENT DOCUMENTS

| | | | | |
|---|---|---|---|---|
| 5,833,714 | A * | 11/1998 | Loeb | 607/56 |
| 6,600,956 | B2 * | 7/2003 | Maschino et al. | 607/118 |
| 6,671,561 | B1 * | 12/2003 | Moaddeb | 607/120 |
| 6,907,295 | B2 * | 6/2005 | Gross et al. | 607/118 |
| 7,881,808 | B2 * | 2/2011 | Borgaonkar et al. | 607/122 |
| 2003/0040785 | A1 * | 2/2003 | Maschino et al. | 607/118 |
| 2007/0060815 | A1 * | 3/2007 | Martin et al. | 600/372 |
| 2008/0208300 | A1 | 8/2008 | Pasch | |

* cited by examiner

*Primary Examiner* — Michael Kahelin
*Assistant Examiner* — Mallika D Fairchild
(74) *Attorney, Agent, or Firm* — Tarolli, Sundheim, Covell & Tummino LLP

(57) ABSTRACT

Example ionic coupling electrodes are described. One example ionic conducting electrode includes a first portion that can be coupled to a single phase current source. The first portion carries current flow via electrons. The electrode includes a second portion to apply a current to a nerve tissue. The second portion carries current flow via ions. The second portion is positioned between the nerve tissue and the first portion to prevent the first portion from touching the nerve tissue. The current applied to the nerve tissue is produced in the second portion in response to a current that is present in the first portion. The current present in the first portion is provided from a single phase current source. The electrode may be used in applications including, but not limited to, nerve block applications and nerve stimulation applications.

9 Claims, 10 Drawing Sheets

SEPARATED-INTERFACE NERVE ELECTRODE

PRIORITY CLAIM

This application claims the benefit of U.S. Provisional Application 61/263,592, filed Nov. 23, 2009.

FEDERAL FUNDING NOTICE

The invention was developed with federal funding supplied under Federal Grant No. R01-EB-002091 provided by the National Institute of Biomedical Imaging and Bioengineering of the National Institute of Health. The Federal government has certain rights in the invention.

BACKGROUND

Conventional electronic coupling electrodes have produced undesired side effects in nerve blocking and nerve stimulating applications. The undesired side effects may include, for example, tissue damage. The damage may occur, for example, due to the fact that conventional electrodes carry current via electrons while nerve tissues carry current via ions. (See, for example, Krames, Elliot S., Neuromodulation, Academic Press, 072009. 152.) Delivery of DC through standard platinum electrodes has produced signs of tissue damage within 20 seconds and therefore is not a practical solution for chronic human use.

Undesired or pathological hyperactivity in the peripheral nervous system occurs in many disorders and diseases. This undesired or pathologic hyperactivity may result in undesired motor or sensory effects. Additionally, some medical conditions resulting in chronic pain (e.g., neuromas) are characterized by undesired afferent activity in peripheral nerves. Treatment may include blocking the conduction of these pathological or undesirable signals to mitigate the effects of these conditions. However, conventional conduction blocks may have employed conventional electrodes that lead to undesired side effects.

Uncoordinated or unwanted generation of nerve impulses is a major disabling factor in many medical conditions. For example, uncoordinated motor signals produce spasticity in stroke, cerebral palsy and multiple sclerosis, resulting in the inability to make functional movements. Involuntary motor signals in conditions such as tics and choreas produce incapacitating movements. Undesirable sensory signals can result in peripherally generated pain. Over-activity in the autonomic nervous system can produce conditions such as hyperhydrosis. If these nerve impulses can be interrupted along the peripheral nerves in which they travel, these disabling conditions can be managed or eliminated.

Conventional nerve blocks that prevent the propagation of an action potential through a nerve have been achieved using high frequency alternating current (HFAC), using single phase current (e.g., direct current), and through combinations thereof. HFAC, where the frequency ranges between, for example, 2 kHZ and 50 kHZ, can completely yet reversibly block the motor fibers in a peripheral nerve. In a conventional nerve blocking apparatus, HFAC is typically delivered through one or more conventional electrodes, which has provided sub-optimal results due, at least in part, to the design of the conventional electrodes.

Conventional nerve blocking has also been achieved by applying a prolonged single phase current to a nerve. The single phase current can be, for example, a direct current (DC). Conventional attempts to apply prolonged DC to a nerve have also lead to tissue damage.

A conduction nerve block that does not generate an onset response has been achieved through a combination of direct current and HFAC. Once again, conventional attempts to apply either HFAC and/or prolonged DC to a nerve have produced tissue damage.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
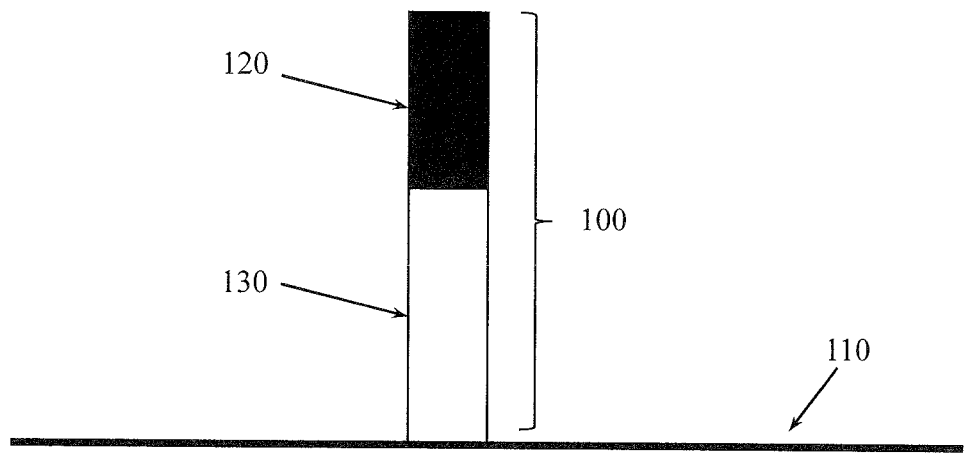
FIG. 1 illustrates two embodiments of an example separated-interface nerve electrode.
Figure 1:
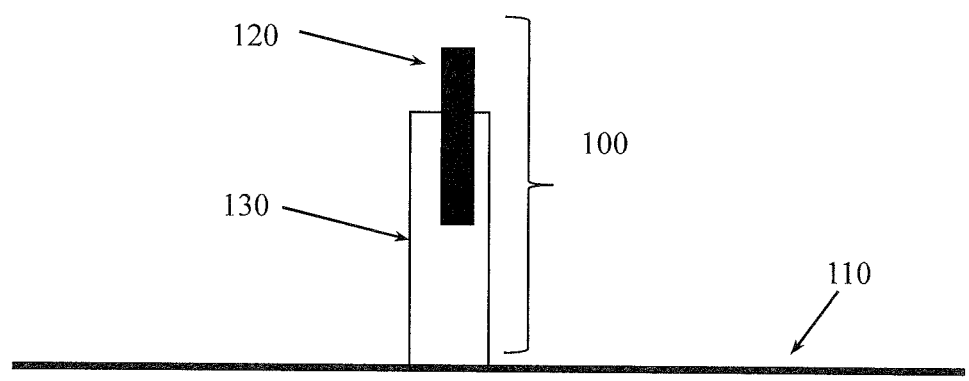

This application describes ionic coupling electrodes. In one embodiment, an ionic coupling electrode facilitates a single phase current nerve blocking application. In another application, an ionic coupling electrode facilitates a single phase current nerve stimulating application. The ionic coupling electrodes facilitate applying a prolonged single phase current to a nerve while mitigating nerve damage associated with conventional approaches.

"Ionic coupling", as used herein refers to being conductive to ionic current flow. Conventionally, electrical stimulation is delivered using metal electrodes. The metal electrodes carry current as the flow of electrons. However, nerve tissues in the body carry current as the flow of ions. Therefore, conventionally, there has been an interface between a metal electrode that is carrying current as an electron flow and a nerve tissue that is carrying current as an ion flow. (See, for example, Krames, Elliot S. Neuromodulation, Academic Press, 072009, 152) This interface has been the source of sub-optimal results. In some embodiments, this electron/ion interface has yielded sub-optimal results including tissue damage.

To mitigate this tissue damage, example ionic coupling electrodes do not contact nerve tissue with a component that carries current as an electron flow. Instead, example ionic coupling electrodes contact the nerve tissue with a component that carries current as an ionic flow. Example ionic coupling electrodes have an electron current flow to ion current flow interface spaced apart from the nerve and have a separate ion current flow to ion current flow interface.

In one embodiment, an electrode separates the electrode interface from the tissue through an intervening aqueous electrolytic interface. This ionic coupling electrode may be referred to as a "Separated-Interface Nerve Electrode" (SINE). In one example, the SINE is configured to produce a low duty-cycle DC that will damage neither the tissue nor the electrode. In one example, the ionic coupling electrode will deliver DC to a nerve through an aqueous electrolytic interface. In one example, an ionically conductive medium may be a conductive electrolytic media.

One example electrode interfaces to a nerve through an ionically conductive medium (ICM). In one example, the ICM (e.g., gel, liquid, solid, polymer, film) may be placed in contact with nerve tissue. In another example, the ICM, which may be, for example, a conductive electrolytic media (e.g., saline), may not come in direct contact with the nerve tissue but instead may be separated from the nerve tissue by a membrane interface. The ICM may also be placed in contact with a traditional metal interface (e.g., platinum) or a capacitive electrode interface (e.g., Tantalum). The traditional interface or capacitive electrode interface can then in turn be connected to a lead wire and then to a single phase current source. The single phase current source may be, for example, a DC source. A current in the traditional interface or capacitive electrode interface can be used to produce a current in the ICM. The current in the ICM can then be applied to the tissue.

The ICM may be contained in a structure (e.g., tube). The structure may have a hole or opening through which the ICM can contact the nerve tissue. The structure may include one or more compartments or portions that contain ICMs. Different compartments may contain different ICMs. For example a first compartment may have a liquid, a second compartment may have a solid, a third compartment may have a polymer, and a fourth compartment that is in contact with the nerve may have a gel. The compartments may be separated by a physical barrier that is conductive to ionic current flow but not to harmful elements generated at a metal interface.

The single or multiple compartments hold the ICM. The ICM receives inputs from a lead. In one example the ICM can be directly connected to the lead. In another example, the ICM is indirectly connected to the lead by a capacitive interface. In one example, the capacitive interface could even be placed in the ICM. In this example, the surface area of the capacitive interface could be large relative to the size of a conventional electrode-tissue interface. In this example, a capacitive only transduction of charge from the lead to the ICM could occur. In another example, a mostly capacitive transduction of charge could also occur between the lead and the ICM. As the surface area increases, a large capacitive charge transfer can occur without requiring a large compliance voltage.

Conventional contact points may have been compromised by the presence and/or creation of harmful elements produced where a conventional electrode touches a nerve during application of current. By way of illustration, a harmful element may be generated at a metal interface between an electrode and nerve tissue during stimulation. Stimulation-induced damage may be due to deleterious electrochemical reaction products generated from reduction/oxidation reactions at the site of the electrode. If toxic products that are produced at the electrode-electrolyte interface are prevented from reaching the nerve, then conventional negative results associated with DC delivery may be mitigated.

Therefore, in one example, the ICM may include elements that impede the movement of harmful species generated at a metal interface to nerve tissue. The movement impeded may be diffusive movement or other movement. The metal interface may be, for example, an impeding matrix or barrier. In one embodiment, the ICM may be a material that reacts with and neutralizes harmful elements generated at the neural interface. In another embodiment, the ICM may include elements that react with and neutralize harmful elements generated at the neural interface.

While the application refers to "the ionically conductive medium", one skilled in the art will appreciate that in different embodiments the ionically conductive medium may be a combination or mixture of ionically conductive materials.

The electrode can be packaged in different ways. For example, the electrode may take the physical form of a nerve cuff, of a paddle-type electrode, of a cylindrical type electrode, and other forms. The electrode may include two or more electrical interfaces to the nerve tissue. Since example electrodes can take different forms, shapes, sizes, and configurations, it follows that example electrodes can be designed for implantation in the central and/or peripheral nervous systems. Therefore nerves for which the electrode can provide an ionically conducted signal include, but are not limited to, peripheral nerves, spinal nerves, branches of spinal nerves, sub-branches of spinal nerves, cranial nerves, branches of cranial nerves, sub-branches of cranial nerves, a nerve associated with a peripheral plexus, nerves within the central nervous system, and so on.

FIG. 1 illustrates two embodiments of an ionic coupling electrode 100. Electrode 100 includes a first portion 120 and a second portion 130. The first portion 120 is configured to be coupled to a single phase current source. The first portion 120 carries current flow via electrons. The second portion 130 is configured to deliver a current to nerve tissue 110. The second portion 130 carries current flow via ions. Nerve tissue 110 also carries current flow via ions. In some examples, the first portion 120 may act as an electrode and the second portion 130 may act as an electrolyte and the first portion 120 and the second portion 130 may share an electrode/electrolyte interface. The electrode/electrolyte interface may have a larger (e.g., 10×, 100×) surface area than the electrolyte/nerve interface. In the different embodiments, the first portion 120 may be arranged to abut the second portion 130 or may be arranged in or substantially in the second portion 130. One skilled in the art will appreciate that there are different techniques for producing an electrode/electrolyte interface between the first portion 120 and the second portion 130.

In one embodiment, the second portion 130 is configured to be positioned between the nerve tissue 110 and the first portion 120 so that the first portion 120 will provide separation between the first portion 120 and the nerve tissue 110. The separation may be, for example, a physical separation and/or a chemical separation. The second portion 130 is configured to apply a current to the nerve tissue 110. The current applied to the nerve tissue 110 is a current that is produced in the second portion 130 in response to a current present in the first portion 120. In one example, the current may be on the order of 1-10 mA. The current present in the first portion 120 is provided from the single phase current source. In one example, the single phase current source may provide a direct current that is used in a nerve blocking and/or in a nerve stimulating application. In one example, the single phase current source may provide a blocking phase current having a first polarity and may also provide a recovery phase current that is opposite in polarity to the first polarity. This may facilitate avoiding damage at the interface between the electrode 100 and the nerve tissue 110.

The second portion 130 may include an ICM. The ICM may be, for example, a gel, a liquid, a solid, a polymer, and a film. The ICM may be, for example, an aqueous solution (e.g., saline). The first portion 120 may be, for example, a metal portion (e.g., platinum) or a capacitive electrode (e.g., tantalum). One skilled in the art will appreciate that other metals and capacitive elements may be employed. In one example, when the first portion 120 is a capacitive element, the first portion 120 may be positioned in the ICM of the second portion 130.

In one embodiment, the ICM of the second portion 130 may be configured to impede movement of undesired elements that may be generated at an interface between the electrode 100 and the nerve tissue 110. The undesired product may be generated as a result of applying a single phase current to the nerve tissue 110. In another embodiment, the ICM of the second portion 130 may be or may include a material that reacts with and neutralizes the undesired product. The undesired product may be, for example, a deleterious electrochemical reaction product generated from reduction/oxidation reactions at the site of the electrode.

In one embodiment, the second portion 130 may include two or more ICM portions. In different embodiments, only one of the two or more ICM portions may contact the nerve tissue 110 or deliver a current to the nerve tissue 110, more than one member of the two or more ICM portions may contact or deliver current to the nerve tissue 110, and even all the members of the two or more ICM portions may contact or deliver current to the nerve tissue 110.

In one embodiment, members of the two or more portions are separated by a physical barrier that is conductive to ionic current flow. The physical barrier may be configured to prevent conduction of an undesired product generated at an interface between the electrode 100 and the nerve tissue 110 or at an interface between the first portion 120 and the second portion 130. The undesired product may be generated as a result of applying a single phase current to the nerve tissue or as a result of the charge transfer at the electrode/electrolyte interface.

In one embodiment, all the members of the two or more ICM portions are made from the same material. In another embodiment, at least one of the ICM portions is made from a different material than at least one other ICM portion.

Electrode 100 may be configured to be implanted into a human or other animal and to contact a nerve tissue in one of, the central nervous system, and the peripheral nervous system. In different embodiments, the electrode 100 may be configured as a nerve cuff, a paddle type electrode, a cylindrical type electrode, and as other types of electrodes.

More generally, electrode 100 is an ionic coupling electrode that has at least two parts. A first part carries current flow via electrons and a second part carries current flow via ions. The first part is configured to receive a single phase current from a current source and to produce a corresponding current in the second part. The second part is configured to deliver, either directly or indirectly, the corresponding current to a tissue (e.g., nerve) and to keep the first part from contacting the tissue. The interface between the first part and the second part may be referred to as an electrode-electrolyte interface.

In one proto-type example, an electrode-electrolyte interface was achieved using a 2.5 cm long stranded stainless steel wire located in a 25 cc saline-filled syringe. The syringe was connected to a polymer nerve cuff via a 15 cm silicone tube (~1.5 mm inner diameter). The neural interface of the example was a ~1.0 $mm^2$ window in the nerve cuff. The syringe and barrel were filled with 0.9% medical saline to provide a conductive pathway from the metal conductor to the nerve. While a syringe is described, one skilled in the art will appreciate that more generally, a container (e.g., tube) that houses saline or another electrolyte may be employed.

In another general embodiment, electrode 100 is an ionic coupling electrode that has a portion 130 that carries current flow via ions and that has a capacitive interface configured to receive a single phase current from a current source and to produce a corresponding current in the portion 130. The corresponding current is produced through a capacitive transduction of charge and then delivered to a tissue (e.g., nerve) via the portion 130.

The two general embodiments described above reflect that there are two primary mechanisms for electrical charge transfer at the electrode-electrolyte interface between the first portion 120 and the second portion 130. The two primary mechanisms are non-Faradaic charge transfer and Faradaic charge transfer. Non-Faradaic charge transfer is capacitive in nature (e.g., no electron transfer across the electrode/electrolyte interface) and results from a reorganization of charged species in the electrolyte when a potential is placed on the electrode. Faradaic charge transfer results from reduction/oxidation reactions at the electrode surface that involve electron transfer between the electrode and species in the electrolyte. For most commonly used electrode materials (e.g. platinum), charge is transferred using a combination of these two mechanisms. However, several materials which solely utilize non-Faradaic charge transfer have been developed and integrated into neural stimulation electrodes (e.g. titanium nitride). Therefore, as described above, example embodiments may involve Faradaic and/or non-Faradaic charge transfer at the interface between the first portion 120 and the second portion 130.

Electrode materials for the first portion 120 that utilize only non-Faradaic charge transfer are attractive because they prevent toxic species formation at the electrode surface. However, the amount of charge that a non-Faradaic electrode can deliver for a given electrode voltage is proportional to its surface area. By separating the electrode-electrolyte and nerve interfaces using the SINE architecture, a large charge transfer surface area can be achieved while maintaining the small surface area desired for the electrode-nerve interface. A large surface area can be gained by using materials that have a high surface area to geometric area ratio such as materials that are highly porous and/or that have small (e.g., submicron) particle size. One DC electrode design involves maximizing the amount of capacitive charge transfer per unit surface area. In one example, the electrode material of the first portion 120 is a porous carbon material. Another approach to gaining a large surface area is to utilize the entire lead structure to create a large interface between the electrode and electrolyte.

In one embodiment, the electrode material of the first portion 120 may include an electrochemical double layer capacitor (EDLC) coating consisting of 60 wt % Cabot "Black Pearls 2000" and 40 wt % DuPont Nafion. Black Pearls 2000 is a high surface area (about 1000 $m^2/g$), carbon with high electrical conductivity. The Nafion acts as both a binder to hold the carbon particles together and as an electrolyte within the EDLC film. The EDLC may be formed by painting a thin layer of a BP2000/Nafion suspension in alcohol onto a graphite rod (¼" dia.). A total dry film weight of 15 mg (9 mg of carbon, 6 mg of Nafion) and a geometric area of the coating of 1 $cm^2$ may be employed. One example EDLC film with a capacitance of ≈170 mF may be employed. When this film is charged and discharged under suitable conditions (e.g., trickle charging at +67 pA for 5 minutes, discharging at −2 mA for 10 s), the electrode potential varies by only 110 mV, and the potential is well within the window of electrochemical stability of water (ca. −0.2V to +1.0V for this electrolyte and reference electrode).

In one embodiment, the first portion 120 may include a lead wire whose end is coated in a thin film of high surface area material. In this embodiment, the lead wire material may also be in contact with the electrolyte of the second portion 130 and may undergo the same potential variations as the electrode. Therefore, in one embodiment, the lead wire may be extended with a length of a highly corrosion resistant metal (e.g., platinum). In this embodiment, the platinum wire acts as the core of the electrode and is coated with the high surface area material.

Turning now to the ICM of the second portion 130, the ICM may be an electrolyte. The electrolyte will be configured to have high ionic conduction, long-term stability, and biocompatibility. Viscous electrolyte gels may facilitate impeding the movement, either diffusive or otherwise, of chemical species generated at the electrode/electrolyte interface. In one example, the electrolyte may include a gel filler material. The gel filler material may be, for example, biocompatible polymeric gels including calcium alginate or polyvinyl alcohol. In one example, where the gel filler is a hydrophilic material like polyvinyl alcohol, salts can be incorporated to provide desired ionic conductivity.

Figure 2:
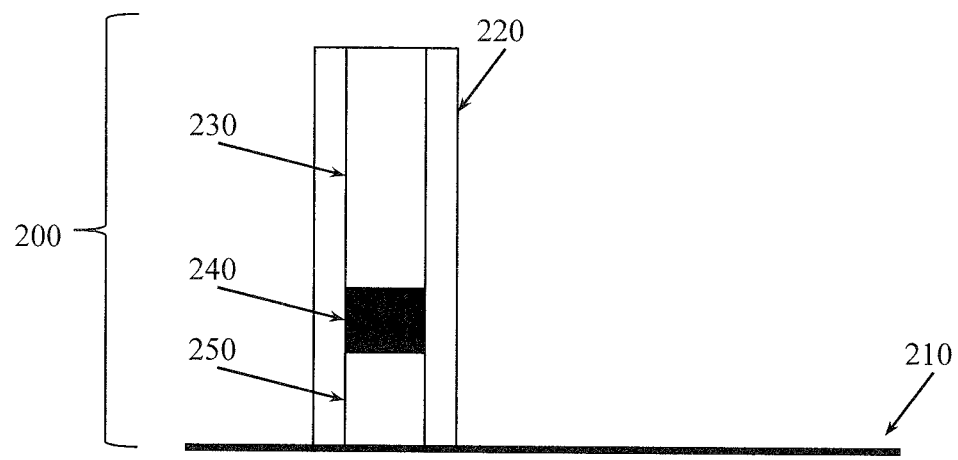
FIG. 2 illustrates an example separated-interface nerve electrode.

FIG. 2 illustrates a first embodiment of a nerve cuff electrode 200 interfacing with a nerve 210. The nerve cuff electrode 200 includes an insulator 220 for a lead that will provide a signal. The nerve cuff electrode 200 also includes a conductor 230 for the signal. The conductor 230 conducts the signal to a metal portion 240 of the nerve cuff electrode 200. The metal portion 240 is in contact with an ICM 250 that is in turn in contact with the nerve 210. Thus, rather than a metal lead contacting the nerve 210, an ICM (e.g., gel, film, liquid) contacts the nerve 210. This facilitates mitigating nerve damage issues associated with conventional metal to tissue contact electrodes.

Figure 3:
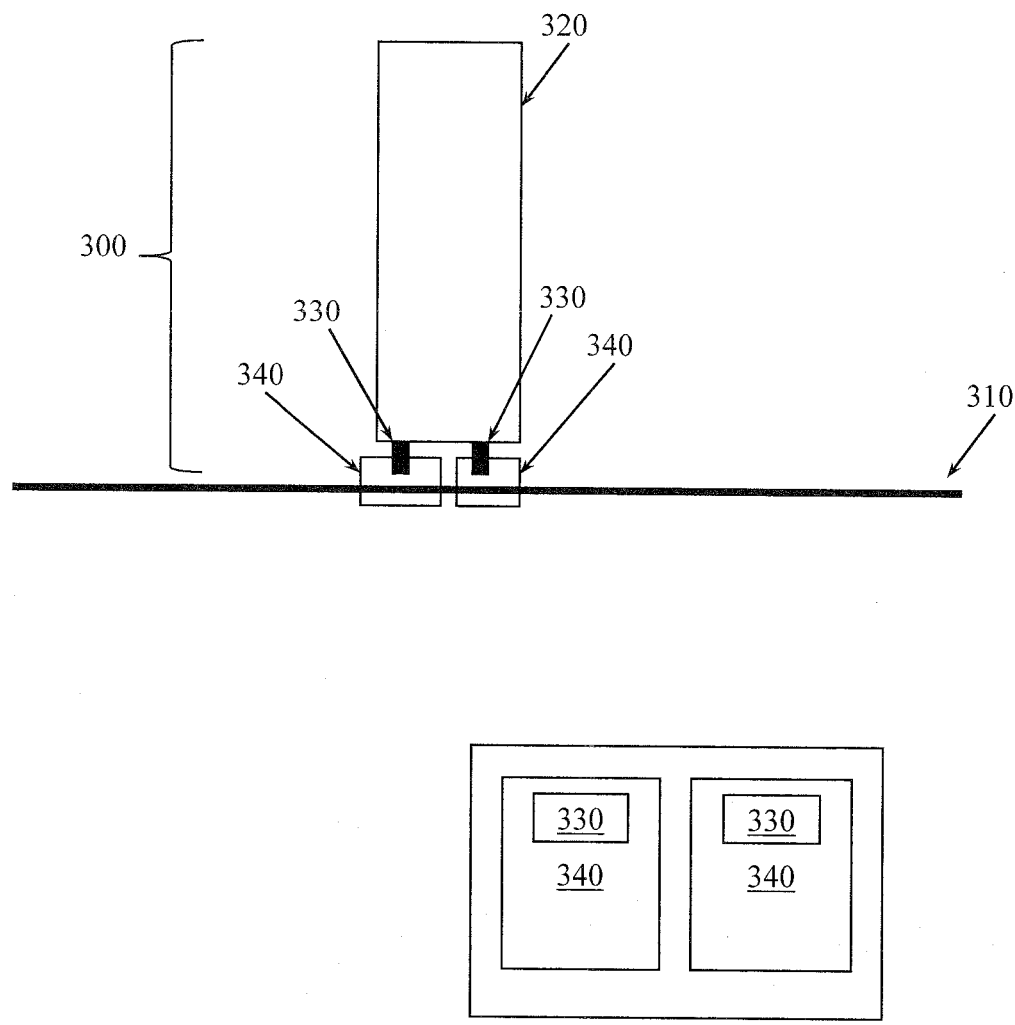
FIG. 3 illustrates an example separated-interface nerve electrode.

FIG. 3 illustrates a second embodiment of a nerve cuff 300 interfacing with a nerve 310. Nerve cuff 300 includes a lead 320 that terminates at two metal contacts 330. The metal contacts 330 are in touch with two portions 340 of an ICM. In the top portion of FIG. 3 the nerve cuff 300 is illustrated encircling nerve 310. In the bottom portion of FIG. 3 the nerve cuff 300 is illustrated "unrolled". While FIG. 2 illustrated one portion of ICM, FIG. 3 illustrates two portions 340 of ICMs. One skilled in the art will appreciate that an electrode can include one or more portions of ICMs.

Figure 4:
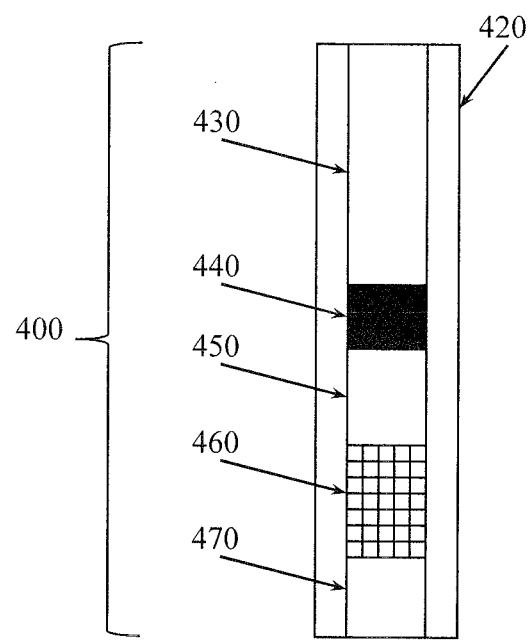
FIG. 4 illustrates an example separated-interface nerve electrode.

FIG. 4 illustrates a first embodiment of a cylindrical electrode 400. Electrode 400 includes an insulator 420 that insulates a conductor 430 that terminates at a metal contact 440. Metal contact 440 is in contact with an ICM 450. Electrode 400 includes another ICM 470 that is separated from medium 450 by an insulating separator 460. While two ICM portions 450 and 470 are illustrated, a greater number of ICM portions may be employed. In one embodiment, a current in one ICM portion is used to produce a current in a neighboring, downstream portion. For example, a current in ICM 450 can be used to produce a current in ICM 470.

Figure 5:
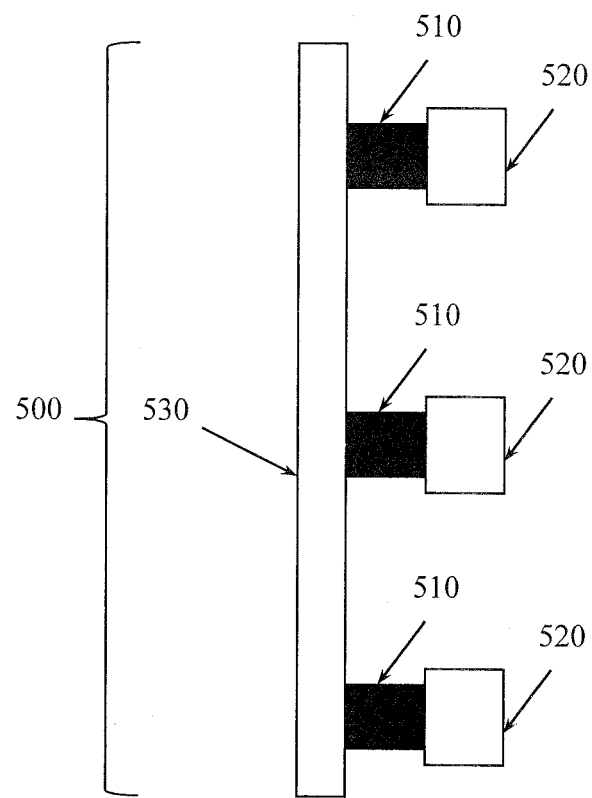
FIG. 5 illustrates an example separated-interface nerve electrode.

FIG. 5 illustrates a second embodiment of a cylindrical electrode 500. Cylindrical electrode 500 is illustrated having three metal contacts 510 and three separate ICMs 520. Lead 530 provides a signal or signals to contacts 520. The signal may be, for example, a single phase current. Insulators and other pieces are not illustrated in electrode 500. While three metal contacts 510 and three ICMs 520 are illustrated, one skilled in the art will appreciate that a greater and/or lesser number of contacts and ICMs may be employed. In one embodiment, all the contacts will be identical and all the ICMs will be identical. In another embodiment, both the contacts and the ICMs may differ. For example, a first smaller contact may interface with a gel while a second larger contact may interface with a polymer. One skilled in the art will appreciate that various combinations can be employed.

Figure 6:
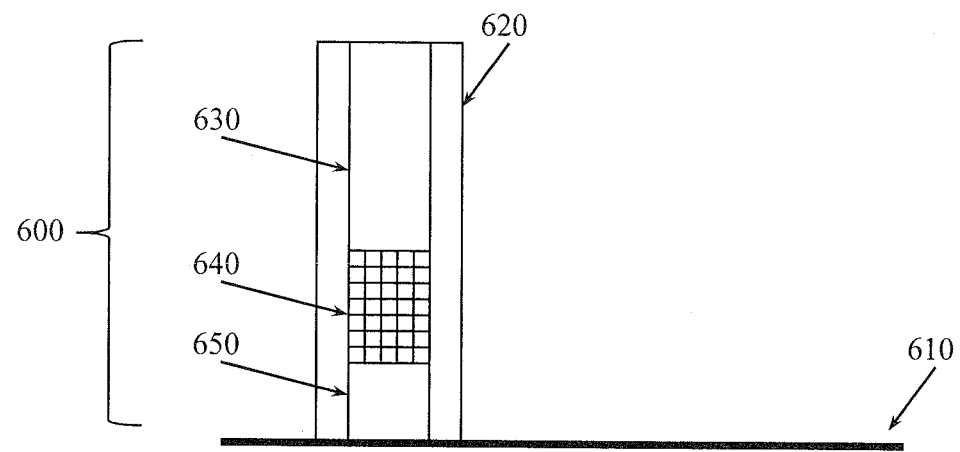
FIG. 6 illustrates an example separated-interface nerve electrode.

FIG. 6 illustrates a first embodiment of a nerve cuff electrode 600 interfacing with a nerve 610. The nerve cuff electrode 600 includes an insulator 620 for a lead that will provide a signal. The nerve cuff electrode 600 also includes a conductor 630 for the signal. The conductor 630 conducts the signal to a capacitive interface portion 640 of the nerve cuff electrode 600. The capacitive interface portion 640 is in contact with an ICM 650 that is in turn in contact with the nerve 610. Thus, rather than a capacitive interface 640 contacting the nerve 610, an ICM (e.g., gel, film, liquid) contacts the nerve 610. This facilitates mitigating nerve damage issues associated with conventional metal to tissue contact electrodes.

Figure 7:
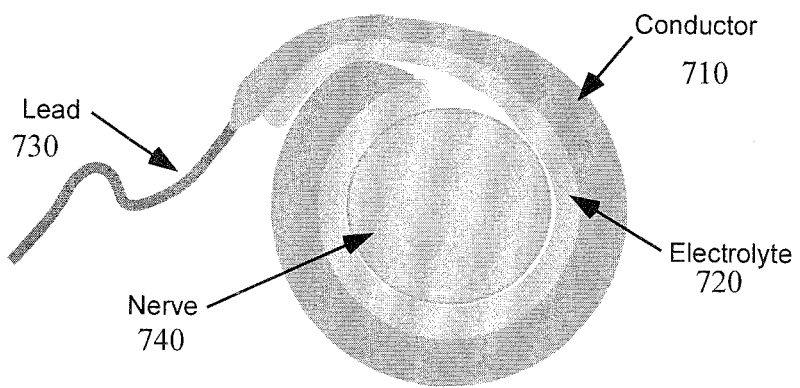
FIG. 7 illustrates an example separated-interface nerve electrode.

FIG. 7 illustrates a nerve 740 that is partially wrapped by an electrolyte 720 that is in touch with a conductor 710. The conductor 710 is provided with a single phase current from a lead 730. In one embodiment, the electrolyte 720 provides a separation between the conductor 710 and the nerve 740. The separation may be, for example, a physical separation and/or a chemical separation. In one example, the surface area where the conductor 710 and the electrolyte 720 are in contact is larger than the surface area between the electrolyte 720 and the nerve 740. The difference in surface area may be extreme. For example, in one embodiment the difference in surface area may be one order of magnitude (e.g., 10×) while in another embodiment the difference in surface area may be two or more orders of magnitude (e.g., 100×). In one example, the current delivered may be on the order of 1-10 mA.

Figure 8:
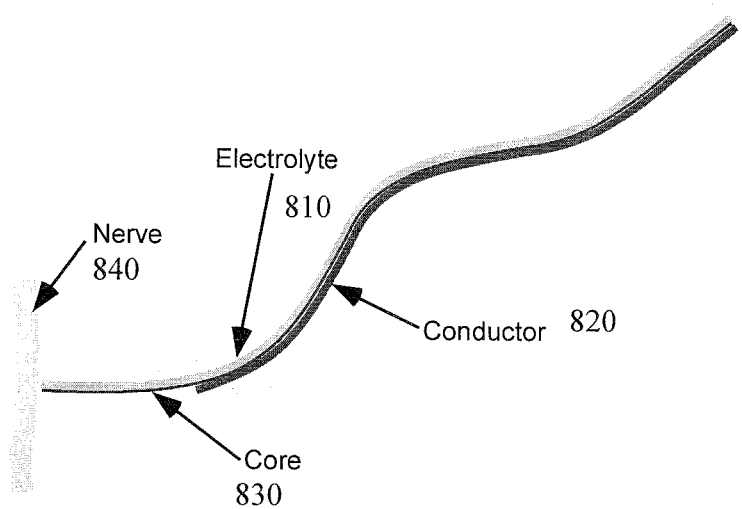
FIG. 8 illustrates an example separated-interface nerve electrode.
Figure 9:
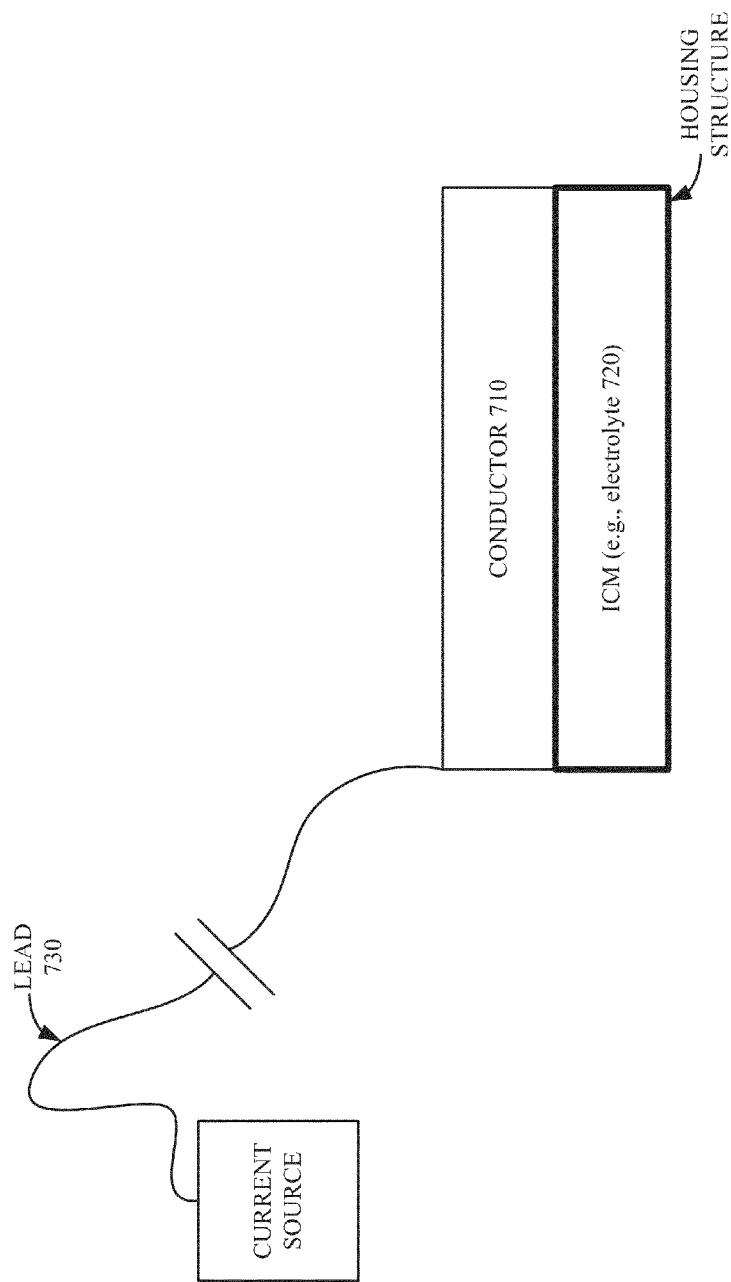
FIG. 9 illustrates another example of a separated-interface nerve electrode.
Figure 10:
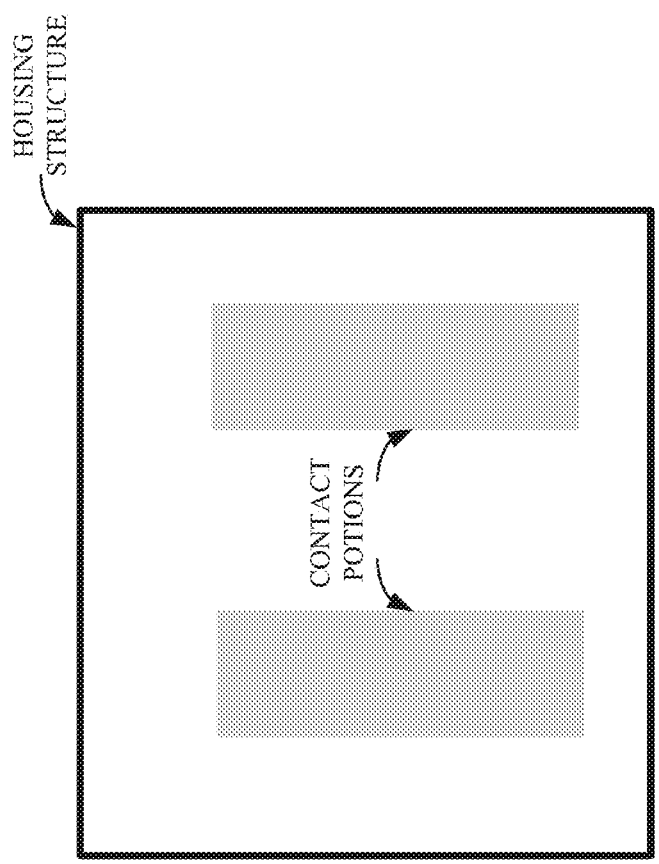
FIG. 10 illustrates a bottom view of a housing structure comprising an example membrane interface.

FIG. 8 illustrates a nerve 840 to which a current may be applied by an electrolyte 810. A current will be produced in electrolyte 810 by its interface with conductor 820 and/or core 830. In this example, the electrode/electrolyte interface comprises a lengthy interface that covers a length of the conductor 820 and/or core 830. One skilled in the art will appreciate, therefore, that the electrode/electrolyte interface is much larger than the electrolyte/nerve interface.

In one example, a separated interface electrode will be designed to have drastically different surface areas between the two interfaces (electrode-electrolyte and electrolyte-nerve). FIG. 8 illustrates one embodiment where the entire lead (e.g., conductor 820 and core 830) is used to create a large electrode-electrolyte interface, which then terminates into a very small electrolyte-nerve interface. The large electrode-electrolyte interface means that the reactions there are low and quite possibly reversible and safe. The small electrolyte-nerve interface means high charge density and high effectiveness regarding the impact on the nerve. The electrolyte/nerve interface may be safe to the nerve tissue because of the benign nature of the electrolyte.

A chemical reaction may occur as a result of producing the current in the electrolyte and/or as a result of applying the current to the nerve. Therefore, a separated interface electrode may include a material that is designed and engineered to keep an undesired product generated by the chemical at a close enough physical proximity to the electrode/electrolyte interface or to the electrode where a reverse polarity current can reverse the chemical reaction that produced the undesired product. Additionally, and/or alternatively, the separated interface electrode may include a material that is designed and engineered to keep an undesired product at a close enough physical proximity to the electrode/electrolyte interface or to the electrode so that the chemical reaction is reversible.

The electrodes described in figures one through eight may be employed in a direct current nerve block technique. The nerve block technique may include suppressing conduction in a nerve by applying a direct current block through a separated-interface nerve electrode having an electrode-electrolyte interface separated from an interface between the separated-interface nerve electrode and the tissue (e.g., nerve). The direct current block and the separated-interface nerve electrode are configured to facilitate recovery of conduction in the nerve substantially instantaneously after removal of the direct current block. The direct current block and the separated-interface nerve electrode are also configured to facilitate complete recovery of conduction in the nerve within one minute after removal of the direct current block. In one embodiment, the direct current block and the separated-interface nerve electrode are configured to create a buildup of potassium in the periaxonal space in the nerve.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the invention is not limited to the specific details, the representative apparatus, and illustrative examples shown and described. Thus, this application is intended to embrace alterations, modifications, and variations that fall within the scope of the appended claims.

To the extent that the term "includes" or "including" is employed in the detailed description or the claims, it is intended to be inclusive in a manner similar to the term "comprising" as that term is interpreted when employed as a transitional word in a claim.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A system configured to deliver a monophasic current to a nerve, the system comprising:
   a current source adapted to generate a monophasic electrical current;
   an electrical lead adapted to carry the monophasic current from the current source to a metal conductor of a nerve cuff electrode,
   the nerve cuff electrode, comprising:
      the metal conductor connected to the electrical lead to receive the monophasic electrical current pulse from the current source;
      an aqueous ionically conductive medium (ICM) that separates the nerve and the metal conductor to prevent damage due to an electrochemical reaction product; and
      a housing structure that is physically coupled to the metal conductor and adapted to hold and enclose the ICM.

2. The nerve cuff electrode of claim 1, wherein the monophasic electrical current pulse comprises a constant amplitude between 1 and 10 mA.

3. The system of claim 1, wherein the housing structure comprises a tube.

4. The system of claim 1, wherein the housing structure comprises area that exposes the ICM covered by a membrane interface.

5. The system of claim 4, wherein the membrane interface comprises an ionomer.

6. The system of claim 5, wherein the ionomer comprises polytetrafluoroethylene-co-perfluoro-3,6-dioxa-4-methyl-7-octenesulfonic acid.

7. The system of claim 1, wherein the monophasic electrical current produced by the current source comprises a DC current.

8. The system of claim 1, wherein the monophasic electrical current produced by the current source comprises an amplitude of between 1 mA and 10 mA.

9. The system of claim 1, wherein the ICM comprises a material that at least one of reacts with and neutralizes the electrochemical reaction product.

* * * * *